United States Patent [19]

Wretlind et al.

[11] Patent Number: 5,093,044
[45] Date of Patent: Mar. 3, 1992

[54] TRIGLYERCIDE NUTRIENT FOR HUMANS AND ANIMALS

[75] Inventors: Arvid Wretlind, Stockholm; Bengt Ajaxon, Uppsala, both of Sweden

[73] Assignee: Kabivitrum AB, Stockholm, Sweden

[21] Appl. No.: 488,010

[22] PCT Filed: Sep. 6, 1989

[86] PCT No.: PCT/SE89/00474
§ 371 Date: Jun. 27, 1990
§ 102(e) Date: Jun. 27, 1990

[87] PCT Pub. No.: WO90/02549
PCT Pub. Date: Mar. 22, 1990

[30] Foreign Application Priority Data
Sep. 7, 1988 [SE] Sweden ................... 8803141

[51] Int. Cl.$^5$ .............................. C11C 3/02
[52] U.S. Cl. ................................. 260/410.7

[58] Field of Search ............ 514/23, 724; 424/312; 260/410.7

[56] References Cited
U.S. PATENT DOCUMENTS
4,665,057  5/1987  Nelson et al. ............ 514/546
4,701,443 10/1987  Nelson et al. ............ 514/23

Primary Examiner—Jose G. Dees
Assistant Examiner—Deborah D. Carr
Attorney, Agent, or Firm—Pollock, Vande Sande and Priddy

[57] ABSTRACT

The invention relates to a nutrient for humans and animals, which is characterized in that the nutrient contains at least one non-readily water-soluble glyceride of at least one keto acid or hydroxy acid. The nutrient can be administered together with food, or in the form of an emulsion of the glyceride.

20 Claims, No Drawings

TRIGLYERCIDE NUTRIENT FOR HUMANS AND ANIMALS

Quantitatively speaking, the most important nutrients in food for both the human and animal species are water, protein, carbohydrates and fats. The three last mentioned nutrients are burned in the body, therewith producing energy. The most important function of the protein, however, is not to provide an energy source, but to provide the body with amino acids for building-up and retaining body proteins. Carbohydrates and fat, on the other hand, function mainly as energy sources. Only a small part have significance in building-up different functional parts of body tissues. In addition to fats and carbohydrates, there are a number of other substances which can be burned by the body and therewith provide a not insignificant energy boost. Such substances include ethyl alcohol and sugar alcohols, such as sorbitol, xylitol and glycerol.

In the metabolism of the body, there are synthesized from carbohydrates and fats a number of metabolites which undergo further oxidation and therewith produce varying amounts of energy. Examples of such metabolites are pyruvic acid ($\alpha$-ketopropionic acid), lactic acid ($\alpha$-hydroxy propionic acid), acetic acid ($\beta$-keto butyric acid) and $\beta$-hydroxy butyric acid. The two latter metabolites are known as ketone bodies. They are formed in large quantities in conjunction with states of starvation. Ketone bodies are formed from acetate groups derived from the decomposition of the fatty acids via $\beta$-oxidation. Further oxidation of the ketone bodies, and therewith the production of energy, diminishes the glucose requirement of several tissues. This results, in turn, in a reduction in the production of glucose from amino acids obtained by degradation of body protein (gluconeogenesis). The formation and oxidation of ketone bodies thus results in a decrease in the loss of the valuable body protein and in a protein-saving effect. This contributes in prolonging survival under starvation conditions. Another effect ascribed to ketone bodies is the suppression of hunger sensations under starvation conditions. The metabolic changes caused by the formation of ketone bodies in conjunction with starvation of otherwise healthy individuals is generally considered as beneficial.

In the case of starvation or undernourishment associated with difficult traumatic states, burns, etc., the metabolic reaction is different. In situations such as these, the organism loses large quantities of the valuable body proteins, while at the same time the formation of ketone bodies is non-existent or negligible. Several authors have considered this to be strongly detrimental to the organism. Certain authors thus consider that the poor formation of ketone bodies is one explanation of the radical breakdown of body proteins in the case of traumatic injuries. In conditions such as these, it would be desirable to reduce the decomposition of body protein to the lowest possible level.

Many attempts have been made and many discussions held with the intention of finding a method of introducing these ketone bodies and similar compounds into the system, so as, if possible, to influence the metabolism and achieve a protein-saving effect, primarily in respect of trauma. It has also been assumed that a protein-saving effect of this nature would be beneficial in so-called slimming diets. A low-calorie diet which contains ketone bodies would be beneficial from two aspects. A first aspect is that the protein-saving effect of the ketone bodies would counteract the loss of body proteins that normally occurs when the food imbibed provides less energy. If this theory is correct, if would therefore be possible to provide a calorie-lean food or diet in which the fat depots of the body would be reduced without the loss of valuable body protein in the muscle, liver, blood etc. The other benefit afforded by the use of ketone bodies in slimming diets resides in the resultant suppression of hunger sensations. The person concerned would then be able to control his/her food intake more readily and maintain it at a desirable low level.

The possibility of introducing ketone bodies to the system via the intake of food has been limited for several reasons. One reason is that ketone bodies such as aceto-acetic acid and B-hydroxy butyric acid are relatively unstable compounds, which readily decompose at those temperatures at which food is cooked. Furthermore, these ketone bodies, which are acids, must be given in the form of salts. There is therefore a risk of administering excessive quantities of cations, such as sodium and potassium. A further drawback is that the ketone bodies and their salts are soluble in water and increase the osmotic pressure of the foodstuff with associated effects, such as too rapid passage through the intestines and diarrhoea.

As a result of long and systematic investigations concerning the above questions it is now possible, because of the present invention, to provide a method in which stable compounds of ketone bodies can be used as a nutrient. These stable compounds comprise esters of keto or hydroxy acids and glycerol. Because the inventive glycerides are either not-readily soluble in water or will not dissolve in water, they will not exert an osmotic pressure. This diminishes the risk of the negative effects on the intestinal passage that are manifested by water-soluble substances which have an osmotic effect. The other advantage afforded by the use of these glycerides is that the esters possessing the keto and hydroxy acids embraced by the invention do not have an acid group which needs to be neutralized, therewith eliminating presence of sodium or potassium. A further unexpected effect afforded by the conversion of keto and hydroxy acids to glycerol esters is that the esters do not exhibit the same poor temperature stability as the acids. Generally speaking, the aforesaid glycerol esters are able to withstand those temperatures at which food is normally cooked, without decomposing.

The chemical structure of the glycerides embraced by the present invention is as follows:

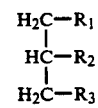

One of the groups $R_1$, $R_2$ or $R_3$ may be a hydroxy group or a residue of a saturated or unsaturated fatty acid that contains 2-24 carbon atoms.

Two or three of the groups $R_1$, $R_2$ or $R_3$ will be one of the following, preferably aliphatic groups deriving from keto or hydroxy acids.

1. Acetoacetate

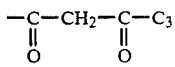

or compounds of the general formula

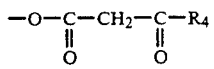

where $R_4$ signifies a straight or branches alkyl chain having 3–6 carbon atoms.

2. Pyreuvat (α-keto propionate)

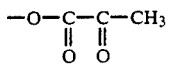

or compounds of the general formula

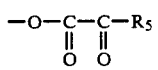

where $R_5$ signifies a straight or branched alkyl chain having 3–6 carbon atoms.

3. β-hydroxy butyrate (β-hydroxy butyric acid)

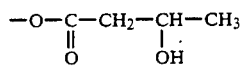

or compounds of the following general formula

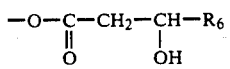

where $R_6$ signifies a straight or branches alkyl chain having 3–6 carbon atoms.

4. Lactate (α-hydroxy propionate)

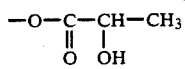

or compounds of the general formula

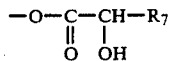

where $R_7$ signifies a straight or branches alkyl chain having 3–6 carbon atoms.

The following are specific examples of glycerides which can be used in nutrients prepared in accordance with the invention:

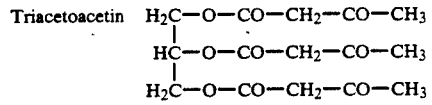

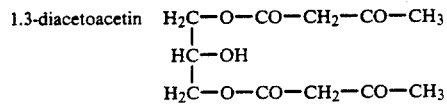

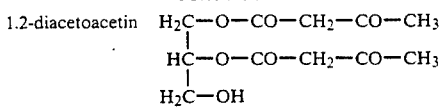

These compounds have the stability desirable for heat sterilization. Subsequent to esterification of the keto acid, there remain no free carboxyl groups which need to be neutralized with sodium or other cations prior to use. Thus, it has been possible to solve the second of the aforesaid problems associated with the use of acetic acid and other keto acids. The glyceride used in accordance with the invention is an oil, and will not dissolve in water, but can be mixed with water without the occurrence of osmotic pressure. One of the hydroxy groups of the glycerol can be esterified with a saturated or unsaturated fatty acid containing 2–24 carbon atoms.

Since triacetoacetin and the majority of other glycerides of keto acids are not soluble in water, must be converted to an emulsion form before they can be infused intravenously. The present invention is the result of extensive development and research work and provides possibilities of producing such stable emulsions of glycerides of the ketone bodies acetic acid and β-hydroxy butyric acid or other α- and β-keto acids. The emulsions have compositions and properties which enable them to be administered to animals and human beings, both enterally and parenterally. Examples of suitable emulsifiers are phospholipids, polyoxyethylene-polyoxypropylene. Tween 80$^R$ (polyoxyethylene(20-)sorbitane monooleate). Ethyl alcohol and glycerol are examples of auxiliary substances that can also be used. These substances are included in the emulsion in varying quantities, depending on the glyceride or glycerides of keto or hydroxy acids used.

The emulsions are prepared in a conventional manner, while observing current pharmaceutical practice in order to obtain an emulsion which is free from side effects. Thus, it is important that the water phase used is sterile and free from pyrogens, and that the emulsifiers and glycerides used are protected against oxidation, for instance by storing said emulsifiers and glycerides under a protective gas.

The inventive emulsions may also contain amino acids, fats, (triglycerides of fatty acids) of synthetic, vegetable or animal origin, carbohydrates, vitamins and mineral substances, in order to enhance the nutrient value.

This enables emulsions to be prepared which can be administered parenterally or enterally for nutrient purposes.

Emulsions constitute a preferred form of preparation of the inventive glycerides suitable for use when, because of illness or injury, a patient is unable to imbibe food in the normal manner. The glycerides, however, may also be used as additions to normal diets or in any other way when the introduction of such glycerides would be beneficial to the patient.

Experiments have indicated that keto and hydroxy acids other than the aforementioned ketone bodies aceto-acetic acid and β-hydroxy butyric acid have protein-saving effects when administered under conditions in which large losses of body protein would otherwise occur. Examples of such compounds include pyruvic acid, (α-keto propionic acid), lactic acid (α-hydroxy propionic acid), levulinic acid (γ-keto valeric acid), α-keto butyric acid, α-keto iso valeric acid, o-keto caproic acid, α-keto isocaproic acid and other keto acids obtained subsequent to deamination of amino acids. Corresponding acids where a hydroxy group has replaced the oxo group (the keto group) also belong to this group of compounds.

Several series of experiments have been carried out on animals in order to determine the tolerance of these glycerides. The glycerides were mixed with the food given to the animals. The tolerance was found to be satisfactory. For example, it was found that the triglyceride of acetoacetate can be given to rats in a 10%-concentration in the food eaten by the rats. This corresponds to about 10 g of triglyceride per kg body weight and day.

The following examples illustrate the preparation of the glycerides used in accordance with the invention and the manner in which they are formed into various nutrient compositions. All percentages relate to weight-/volume percent.

EXAMPLE 1

Glyceryl triacetoacetin (triacetoacetin or TAA) was prepared from glycerol and diketene in accordance with the following reaction formula

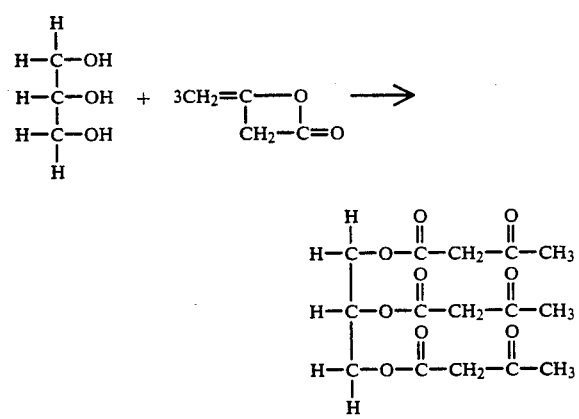

The reaction was carried out by mixing in a reaction vessel, equipped with an agitator or stirring, 92 g of glycerol with sodium acetate and then slowly adding 270 g diketene dropwise. The reaction commenced while generating heat, the temperature being allowed to rise to 120° C. The reaction vessel was then cooled and the reaction temperature maintained at 120° C., while dripping-in the diketene. Subsequent to introducing all of the diketene, the mixture was stirred for 24 hours. The reaction product was dissolved in 500 ml of chloroform, and the solution was washed repeatedly with distilled water, after which the chloroform was evaporated. The residue was checked with respect to purity, with the aid of thin-layer chromatography. The yield was 81.5% triacetoacetin.

EXAMPLE 2

Glyceryl diacetoacetin (diacetoacetin or DAA) was prepared in accordance with the following reaction formula by means of the same method as that used in Example 1.

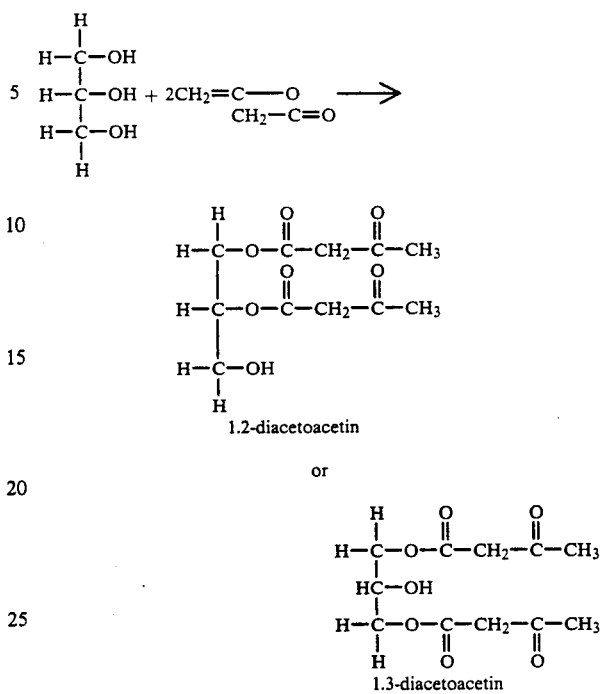

EXAMPLE 3

The compound triacetoacetin prepared in accordance with Example 1 was dispensed into gelatin capsules, or capsules made of some other suitable material. Each capsule contained 0.5 g of the compound. The capsules are intended to be used in quantities of 2–40 capsules per day.

EXAMPLE 4

Triacetoacetin was used to prepare a nutrient preparation containing 5–15% of the compound. The nutrient preparation shall therewith have the following composition, for example:

| | | |
|---|---|---|
| Milk and soya protein | 3.8 | g |
| Triacetoaceton | 5.0 | g |
| Essential fatty acids | 1.6 | g |
| Glucose | 0.1 | g |
| Maltose | 0.4 | g |
| Cane sugar | 3.0 | g |
| Polysaccharides | 10.2 | g |
| Na | 3.3 | mmol |
| K | 3.2 | mmol |
| Cl | <3.3 | mmol |
| Ca | 50 | mg |
| Mg | 13 | mg |
| P | 60 | mg |
| Fe | 1.0 | mg |
| Zn | 0.75 | mg |
| Cu | 0.15 | mg |
| Iodine | 7.5 | µg |
| Water to | 100 | ml |

The nutrient preparation can be augmented with the daily need of water-soluble and fat-soluble vitamins.

The following examples illustrate how the inventive glycerides can be formed into emulsions for parenteral administration of nutrients, primarily intravenous administration. The emulsions can also be administered enterally, if so desired.

EXAMPLE 5

| | |
|---|---|
| Triacetoacetin | 100 g |
| Soybean oil | 100 g |
| Purified egg phosphatide | 50 g |
| Glycerol | 45 g |
| Tween 80 ® | 5 g |
| Sterile water to | 200 ml |
| Sodium hydroxide solution 1 M to pH | 7-10 |

An emulsion was prepared in a conventional manner and then dispensed into 100 ml infusion flasks, and then autoclaved at 120° C. for 20 min.

EXAMPLE 6

| | |
|---|---|
| Triacetoacetin | 40 g |
| Soybean oil | 40 g |
| Purified egg phosphatide | 50 g |
| Glycerol | 22.5 g |
| Ethanol 95% | 80 g |
| Sterile water to | 1000 ml |
| Sodium hydroxide solution to pH | 7-10 |

The emulsion was prepared in a conventional manner. The emulsion was put into 100 ml infusion flasks, which were then autoclaved at 120° C. for 20 min.

EXAMPLE 7

| | |
|---|---|
| Glyceryl monolinolate diacetoacetate | 40 g |
| Soybean oil | 40 g |
| Pure egg phosphatide | 50 g |
| Glycerol | 22.5 g |
| Ethanol 95% | 80 g |
| Sterile water to | 1000 ml |
| Sodium hydroxide solution 1 M to pH | 7-10 |

The emulsion was prepared in a conventional manner. The emulsion was put into 100 ml infusion flasks an autoclaved at 120° C. for 20 min.

We claim:

1. A method for supplying nutrient to a human or animal which comprises administering to said human or animal a nutrient containing an effective nutrient amount of at least one not readily water-soluble glyceride of at least one keto or hydroxy acid, having the formula

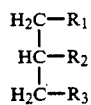

wherein two or three of the groups $R_1$, $R_2$ and $R_3$, independently of each other, are one or more of the groups acetoacetate, alpha-ketopropionate, beta-hydroxybutyrate and alpha-hydroxypropionate, and when only two of the groups $R_1$, $R_2$ and $R_3$ are any of said groups, the third of them is a hydroxy group or a residue of a saturated or unsaturated fatty acid containing 2 to 24 carbon atoms.

2. The method of claim 1 wherein said nutrient contains glyceride in an amount of 0.5 to 100 weight-/volume percent.

3. The method of claim 1 wherein said nutrient contains glyceride in an amount of 2-30 weight/volume percent.

4. The method of claim 1, wherein said nutrient exists in the form of an emulsion of the glycerides in an aqueous phase.

5. The method of claim 4 wherein the emulsion contains at least one member selected from the group of 1-10% ethyl alcohol, 1-20% glycerol, 0.3-4 phospholipids and mixtures thereof.

6. The method of claim 4 wherein said emulsion contains 2-30% of a member selected from the group consisting of soya oil, safflower oil, olive oil, cottonseed oil, sunflower oil, physiologically acceptable triglyceride and mixtures thereof.

7. The method of claim 6 wherein said triglyceride is a triglyceride having a mean-length carbon chain (MCT).

8. The method of claim 4 wherein said emulsion contains 0.5-10% acetylated mono- or diglycerides of saturated or unsaturated fatty acids having 6-24 carbon atoms.

9. The method of claim 4 wherein said emulsion further contains 0.2-10% of a synthetic emulsifier.

10. The method of claim 9 wherein said emulsifier is polyoxyethylene polyoxypropylene.

11. A nutrient for humans and animals in the form of an emulsion containing in the aqueous phase a nutrient effective amount of at least one not readily water-soluble glyceride of at least one keto or hydroxy acid, having the formula

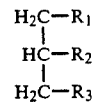

wherein two or three of the groups $R_1$, $R_2$ and $R_3$, independently of each other, are one or more of the groups acetoacetate, alpha-ketopropionate, beta-hydroxybutyrate and alpha-hydroxypropionate, and when solely two of the groups $R_1$, $R_2$ and $R_3$ are any of said groups, the third of them is a hydroxy group or a residue of a saturated or unsaturated fatty acid containing 2 to 24 carbon atoms.

12. The nutrient of claim 11 wherein the nutrient contains said glyceride in an amount of 2-30 weight-/volume percent.

13. The nutrient of claim 11 wherein the emulsion also contains at least one member selected from the group consisting of 1-10% ethyl alcohol, 1-20% glycerol, 0.3-4% phospholipids, and mixtures thereof.

14. The nutrient of claim 11 wherein the emulsion also contains 2-30% of a member selected from the group consisting of soya oil, safflower oil, olive oil, cottonseed oil, sunflower oil, physiologically acceptable triglyceride, and mixtures thereof.

15. The nutrient of claim 11 wherein the emulsion also contains 0.5-10% acetylated mono- or diglycerides of saturated or unsaturated fatty acids having 6-24 carbon atoms.

16. The nutrient of claim 11 wherein the emulsion also contains a synthetic emulsifier in an amount of 0.2-10%.

17. The nutrient of claim 16 wherein said emulsifier is polyoxyethylene polyoxypropylene.

18. The nutrient of claim 16 wherein said triglyceride is triglyceride having a mean-length carbon chain (MCT).

19. A nutrient for a human or animal containing 2–30 weight/volume percent of at least one not readily water-soluble glyceride of at least one keto or hydroxy acid, having the formula

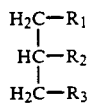

wherein two or three of the groups $R_1$, $R_2$ and $R_3$, independently of each other, are one or more of the groups acetoacetate, alpha-ketopropionate, beta-hydroxybutyrate and alpha-hydroxypropionate, and when solely two of the groups $R_1$, $R_2$ and $R_3$ are any of said groups, the third of them is a hydroxy group or a residue of a saturated or unsaturated fatty acid containing 2 to 24 carbon atoms.

20. The method of claim 1 wherein said nutrient is administered intravenously.

* * * * *